United States Patent [19]

Winnick

[11] 4,207,424
[45] Jun. 10, 1980

[54] CATALYTIC PROCESS FOR DEHYDRATION OF ALCOHOLS

[75] Inventor: Charles N. Winnick, Ridgewood, N.J.

[73] Assignee: Halcon Research & Development Corporation, New York, N.Y.

[21] Appl. No.: 932,243

[22] Filed: Aug. 9, 1978

[51] Int. Cl.$^2$ .................... C07C 15/00; C07C 1/24
[52] U.S. Cl. .................... 585/357; 585/640; 585/437; 585/469
[58] Field of Search .................... 260/669 QZ, 682; 252/455 R, 455; 585/437, 639

[56] References Cited

U.S. PATENT DOCUMENTS

| | | | |
|---|---|---|---|
| 3,526,674 | 9/1970 | Becker et al. | 260/669 QZ |
| 3,780,127 | 12/1973 | Young et al. | 260/682 |
| 3,980,586 | 9/1976 | Mitchell | 252/455 R |
| 4,006,198 | 2/1977 | Tesei et al. | 260/682 |
| 4,052,479 | 10/1977 | Chang et al. | 260/682 |

FOREIGN PATENT DOCUMENTS 43-481   9/1968   Japan ........................ 260/682

*Primary Examiner*—Delbert E. Gantz
*Assistant Examiner*—Joseph A. Boska
*Attorney, Agent, or Firm*—William C. Long; David Dick; Jack B. Murray, Jr.

[57] ABSTRACT

An improved process for the catalytic dehydration of alcohols to form unsaturated organic compounds is provided in which an alcohol is dehydrated in the presence of alumina catalysts which are pre-treated with an organic silylating agent at elevated temperature.

11 Claims, No Drawings

CATALYTIC PROCESS FOR DEHYDRATION OF ALCOHOLS

BACKGROUND OF THE INVENTION

1. Field of the Invention

This invention relates generally to the dehydration of alcohols to form unsaturated organic compounds, and more specifically to an improved dehydration process employing novel silylated dehydration catalysts.

2. Description of the Prior Art

The liquid phase dehydration of aralkanols to aralkenes by the process of U.S. Pat. No. 3,526,674 achieves high aralkanol conversions to aralkene employing a temperature above about 200° C. "High surface area" solids are preferred as dehydration catalysts: these solids are defined as having a surface area in excess of about 15 sq. meters per gram as determined by the Brunauer-Emmett-Teller method. See Smith, Chemical Engineering Kinetics, pages 216–221 (New York, 1956). Activated carbon, natural clays, molecular sieves, silica-aluminas and activated aluminas are exemplified in U.S. Pat. No. 3,526,674 as suitable high surface area solids. Others, such as titania are also useful.

The use of such dehydration catalysts in finely divided form as a suspension of a solids in a liquid phase requires the use of a certain amount of agitation to maintain the suspension. As the power consumed in the operation of agitation devices, in addition to the volume of the liquid (and hence the size of the process equipment) needed to form a slurry, will increase with any increase in the amount of dehydration catalyst employed, any increase of the activity of the dehydration catalyst would permit a decrease in the amount of catalyst used to effect a given conversion and would greatly lower overall processing costs.

Silylated catalysts for the epoxidation of olefins are known from British Pat. No. 1,339,309 to Wulff, in which a solid inorganic oxygen compound of silica in combination with an oxide or hydroxide of titanium, molybdenum, vanadium, zirconium or boron is treated with a silylating agent prior to epoxidation. U.S. Pat. No. 3,980,586 to Mitchell relates to modified refractory metal oxide solids which are sequentially silylated, calcined and steamed to provide compositions which are stated to be suitable catalysts in hydrocracking, alkylation, dealkylation, transalkylation, isomerization, hydrogenation, dehydrogenation, dehydrohalogenation and dehydrocyclization. However, the catalysts and process of British Pat. No. 1,339,309 and U.S. Pat. No. 3,980,586 are not readily adaptable for use in an alcohol dehydration process.

SUMMARY OF THE INVENTION

According to the present invention, an improved process for dehydrating alcohols to form unsaturated organic compound is provided in which the dehydration is effected in the presence of a silylated dehydration catalyst, formed by contacting an alumina with an organic silylating agent at elevated temperature.

The novel silylated dehydration catalysts of this invention have been surprisingly found to exhibit markedly improved dehydration activity as compared to the nonsilylated catalysts heretofore employed for such dehydrations. The greatly improved activity possessed by these catalysts thus enables use of much smaller amounts of catalyst in the dehydration process, thereby resulting in very significant reductions in the attendant equipment, solids handling and catalyst inventory expenses which are associated with the use of larger amounts of catalyst in any dehydration of such alcohols.

DETAILED DESCRIPTION OF THE INVENTION (a) Preparation of the Silylated Dehydration Catalyst The improved dehydration catalysts of the present invention are prepared by contacting a high surface area alumina with a silylating agent at elevated temperature. By "high surface area" is meant a surface in excess of about 15 sq. meters per gram, and desirably in excess of 25 sq. meters per gram as determined by the Brunauer-Emmett-Teller method; see Smith, Chemical Engineering Kinetics, pgs. 216–221, New York (1955). Especially preferred are aluminas having surface areas in the range of about 40 to 250 sq. meters per gram. The aluminas which can be so treated can be in a hydrated or nonhydrated form. Exemplary of suitable aluminas, therefore, are gamma-alumina, eta-alumina, delta-alumina, theta-alumina and the like, with gamma-alumina being especially preferred.

As used herein, the term "alumina" is intended to refer to materials containing at least 75 wt. % $Al_2O_3$. In general, aluminas containing at least 85 wt. % $Al_2O_3$ are preferred, with aluminas containing at least 90 wt. % $Al_2O_3$ being particularly preferred.

Substantially any alumina of the aforementioned surface areas can be used; however, it is especially desired to use those aluminas having low alkali and alkaline earth metal contents as well as low iron contents, since the presence of such impurities increases both formation of by-products and high-boiling residue. Aluminas having combined alkali and alkaline earth metal contents below about 2000 ppm (by weight) and iron contents below about 2000 ppm by weight are accordingly preferred. Such aluminas are readily available as articles of commerce and typical characteristics of some of the commercially available ones most suitable for use in the process of this invention are given in Table I.

TABLE I

| Supplier & Trade Name | Alcoa[1] "F-1" | Alcoa[1] "H-151" | Davison[2] "991" | Davison[2] "992" | Conoco[3] "Catapal N-1" | Conoco[3] "Catapal N-2" | Conoco[3] "Catapal SB" |
|---|---|---|---|---|---|---|---|
| $Al_2O_3$ (wt. %) | 92 | 90 | 65 | 97 | 75 | 75 | 74.2 |
| Volatile content (wt. %)[4] | 6.5 | 6.0 | 35 | 3 | 25 | 25 | 25.8 |
| $SiO_2$ | .09 | 1.7 | .004 | .004 | 0.01 | 0.01 | 0.008 |
| $Fe_2O_3$ (wt. %) | .08 | .1 | | | 0.01 | 0.01 | 0.005 |
| Alkali Metal (As $Na_2O$, wt. %) | 0.9 | 1.4 | .002 | .002 | 0.01 | 0.01 | 0.004 |
| Alkaline Earth Metal (as CaO, wt. %) | — | — | .015 | .015 | — | — | — |

TABLE I-continued

| | Alcoa[1] | | Davison[2] | | Conoco[3] | | |
|---|---|---|---|---|---|---|---|
| Supplier & Trade Name | "F-1" | "H-151" | "991" | "992" | "Catapal N-1" | "Catapal N-2" | "Catapal SB" |
| Surface Area (sq. meters/gram) | 210 | 390 | 450 | 230 | 150 | 200 | 280 |

[1]Aluminum Company of America.
[2]Davison Chemical Corp., Division of W. R. Grace & Company.
[3]Continental Oil Company.
[4]After calcination at from about 900°–1110° C. Water is the predominant volatile material present.

Silylating agents which are suitable for use in the process of this invention are defined herein as agents capable of binding organo-silicon groups to the alumina catalyst which is employed. Suitable silylating agents are characterized by having at least one hydrocarbon group and at least one functional group bonded to silicon. Therefore, suitable silylating agents include the organo-silanes and-disilanes, organo-siloxanes and-disiloxanes, organo-silylamines and-disilanylamines, and organo-silazanes and-disilazanes, which silicon compounds can be illustrated by reference to formula (I), (II), or (III):

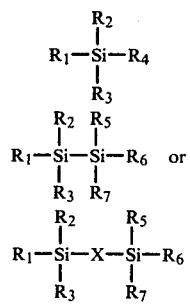

wherein X is oxygen or

and $R_1$, $R_2$, $R_3$, $R_4$, $R_5$, $R_6$ and $R_7$ are independently selected from the group consisting of hydrogen, hydroxy, halogen (e.g., fluoro, chloro, iodo and bromo), alkoxy of from 1 to 8 carbon atoms and preferably from 1 to 4 carbon atoms, alkyl of from 1 to 8 carbon atoms and preferably from 1 to 4 carbon atoms, aryl of from 6 to 12 carbon atoms and preferably from 6 to 8 carbon atoms, alkenyl of from 2 to 8 carbon atoms and preferably from 2 to 5 carbon atoms, alkyl-substituted aryloxy having a total of from 7 to 12 carbon atoms, aryloxy of from 6 to 12 carbon atoms, aryl-substituted alkoxy of from 7 to 12 carbon atoms, alkaryl and aralkyl of from 7 to 12 carbon atoms, amino, acyl of from 1 to 8 carbon atoms and preferably from 1 to 4 carbon atoms, and acyloxy of from 1 to 8 carbon atoms and preferably from 1 to 4 carbon atoms, with the proviso that at least one of $R_1$, $R_2$, $R_3$, $R_4$, $R_5$, $R_6$ and $R_7$ must be alkyl, aryl, aralkyl, alkaryl, alkenyl or acyl, and with the further proviso that if the silicon compound is characterized by formula (I) or (II) above, at least one of $R_1$, $R_2$, $R_3$, $R_4$, $R_5$, $R_6$ and $R_7$ must be hydroxy, halo, alkoxy, alkyl-substituted aryloxy, aryl-substituted alkoxy, aryloxy, amino, acyloxy, or cycloalkoxy. Especially preferred classes of silylating agents are those having formula (I), (II) or (III) above in which X is oxygen or

and $R_1$, $R_2$, $R_3$, $R_4$, $R_5$, $R_6$ and $R_7$ are independently selected from the group consisting of hydrocarbyl of from 1 to 4 carbon atoms, halo and alkoxy of 1 to 6 carbon atoms, with the proviso that at least one of $R_1$, $R_2$, $R_3$, $R_4$, $R_5$, $R_6$ and $R_7$ must be hydrocarbyl and at least one of $R_1$, $R_2$, $R_3$, $R_4$, $R_5$, $R_6$ and $R_7$ must be halo or alkoxy when the silylating agent comprises a compound of formula (I) or (II).

Exemplary of silylating agents therefore are the following: trimethyl ethoxysilane, triethyl methoxysilane, methyl-di(n-propoxy)silane, benzyl-di(n-butoxy)silane, isopropyl triacetoxysilane,

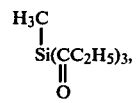

chlorophenylphenoxysilane, tolyldibenzoxysilane, aminopropyltriethoxysilane, vinyltrichlorosilane, trimethylacetoxysilane, dimethyldipropoxysilane, dichlorodimethoxysilane, chlorotrimethoxysilane, N-methyl-3-amino-propyltrimethoxysilane, N-methyl-N-octadecyl-3-aminopropyltriethoxysilane, chlorobromomethoxysilane, chlorodiethylcyclohexoxysilane, iododimethylbutoxysilane, chlorodimethylphenoxysilane, dimethyldiethoxysilane, methyltrimethoxysilane, phenyltrimethoxysilane, dimethyldi(meta-toloxy)silane, sym. tetrachlorodimethoxydisilane, sym. difluorodiphenoxydisilane,

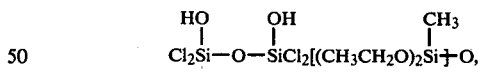

hexamethyldisilazane, sym. tetramethydisilazane, and the like.

The dehydration catalysts of this invention can be formed by contacting the alumina, e.g., gamma-alumina, with the silylating agent, e.g., dimethyldiethoxysilane, at an elevated temperature. For example, alumina can be mixed with the silylating agent in liquid medium and then heated. Satisfactory liquid media include the ethers, aliphatic or aromatic hydrocarbons of 6 to 16 carbon atoms. Thus, the reactants can be charged to the selected liquid medium and heated, e.g., at the reflux temperature of the system, for the desired period of time. Alternatively, the particles of the catalyst may be heated and then contacted with a stream of hot vapor of the silylating agent. The silylation may be carried out as a batch, semi-continuous or continuous process.

The catalyst and silylating agent are preferably contacted at, or heated after contacting to, a temperature in the range of from about 100° to 500° C. with temperatures of from about 200° to 450° C. being preferred. While temperatures outside the foregoing broad range may be used, temperatures of greater than 500° C. are not preferred since side reactions such as cracking can occur. Also, temperatures lower than the above range are less favorable, although they can be employed.

The length of time required for the silylating agent to react with the catalyst depends on the temperature employed, lower temperatures requiring longer reaction times. At a temperature of 350° C., for example, times of from 0.1 to 12 hours are suitable. At a temperature of 200° C., 1 to 36 hours are suitable.

The amount of silylating agent employed can vary widely. Addition to the alumina substrate by the silylation procedure of as little as 0.05 weight percent silicon has been found to enhance the activity of the alumina. However, in general, at least about 0.5 weight % silicon is preferred with at least about 1 weight % being particularly preferred. While silicon can be added to the catalyst in amounts of in excess of 10%, any additional activity enhancement will be generally outweighed by the added costs involved.

The silylating agent can be applied to the catalyst either in one treatment or in a series of treatments. Generally a single treatment is preferred for reasons of manufacturing economy.

When the catalyst is treated with the silylating agent in liquid medium, the silylated dehydration catalyst which is formed can be separated from the liquid medium by known means. Thus, the catalyst may be recovered by standard solids handling techniques, such as filtration, centrifuging or allowing the liquid medium to settle and decanting the liquid.

While any of the aluminas described above, or any similar alumina, can be silylated according to this invention with satisfactory results, even better results are obtained by subjecting the alumina to be silylated to a thermal pre-treatment. This pre-treatment is preferably accomplished by heating the aluminas at a temperature within the range of from about 400° C. to about 850° C. for a time within the range of from 0.5 to 24 hrs., the shorter times being associated with the higher temperatures. Thus, for example, heat-treating of alumina to a temperature of 800° C. for one hour reduces the amount of high-boiling residue made in the dehydration of aralkanols from as much as 5%, without heat treatment, to only 1-1.5% with the heat treatment. Similar reduction in amount of residue made is achieved by heating the alumina for four hours at 450° C.

(b) Use of Silylated Dehydration Catalysts

A wide variety of organic alcohols can be dehydrated by this invention to the corresponding unsaturated organic compounds containing ethylenic unsaturation. Suitable alcohols include alkanols, cycloalkanols and aralkanols, with alkanols and aralkanols being preferred. Thus, the process of this invention is applicable to the production of (1) alkenes by dehydration of the corresponding alkanols, (2) cycloalkenes by dehydration of the corresponding cycloalkanols and (3) styrene and alkyl-substituted styrene by dehydration of the corresponding aralkanols. Suitable aralkanols include alpha-phenylethanol itself, the alpha-alkyl-alpha-phenylethanols and the alkyl ring-substituted derivatives of the foregoing. Suitable aralkanol starting material for the invention have the following structural formula:

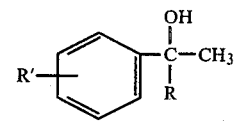

wherein R and R' are each independently selected from the group consisting of hydrogen and lower alkyl radicals, preferably those lower alkyl radicals containing up to three carbon atoms each, although radicals having as many as five carbon atoms each can be employed. It is also possible to employ aralkanol starting materials which have more than one alkyl ring substituent in the process of this invention. It is generally desired to use such aralkanol starting materials having the above structural formula wherein R and R' together have no more than three carbon atoms. Accordingly, preferred aralkanol starting materials include alpha-phenylethanol, alpha-methyl-alpha-phenylethanol (cumyl alcohol), alpha-ethyl-alpha-phenylethanol, alpha-4-methylphenylethanol, alpha-3,5-dimethylphenylethanol, alpha-methyl-alpha 4-isopropylphenylethanol and the like. Especially preferred aralkanol starting materials are alpha-phenylethanol and alpha-methyl-alpha-phenylethanol (cumyl alcohol) since the corresponding aralkene products (styrene and alpha-methylstyrene, respectively) are large scale articles of commerce.

Suitable alkanol starting material include primary, secondary and tertiary aliphatic alcohols, which can contain substitution by non-reactive groups such as halo, (e.g., fluoro, chloro and bromo), nitro and the like. The alkanol will generally have from 2 to 16 carbon atoms, and preferably from 2 to 12 carbon atoms. Exemplary of such alkanols are ethanol, propanol, isopropanol, secondary butanol, tertiary butanol, 2-methyl-2-butanol, 5-methyl-2-hexanol, butenol-3, hexadecanol, and the like. Preferred alkanols in the process of this invention are ethanol, isopropanol and tert-butanol.

Suitable cycloalkanols are those containing from 5 to 16 carbon atoms, preferably from 6 to 12 carbon atoms. Exemplary of cycloalkanols therefore are cyclohexanol, cyclooctanol, cyclododecanol, 2-methyl cyclohexanol, 4-phenyl cyclohexanol, and the like.

Obviously, mixtures of the foregoing alcohols can also be dehydrated and, in such cases, mixtures of unsaturated organic products are obtained.

Pure alcohol feedstocks are not required in the process of this invention; i.e., impurities normally associated with such materials have little or no deleterious effect upon the process. Thus, in the case of alpha-phenylethanol, impurities such as acetophenone, beta-methylbenzyl alcohol, and benzylalcohol can be present in the feed to the dehydration in amounts of as much as 20 to 30% by weight. As will be appreciated by those skilled in the art, such impurities are formed in aralkane oxidations to form the aralkanol and it is a feature of this invention that such impurities need not be removed from the dehydration feed.

The selected alcohol can be dehydrated in the presence of the silylated dehydration catalyst in accordance with the improved process of this invention in either the vapor or liquid phase. Thus, the alcohol may be passed as a vapor over a bed of solid silylated dehydration catalyst. Alternatively, the alcohol and silylated dehydration catalyst may be contacted for dehydration in a liquid medium. The choice of a vapor or liquid dehydration reaction phase will vary widely depending on the alcohol to be hydrated, the silylated dehydration catalyst employed, the desired temperature and pressure and other factors. Thus, for lower alcohols, e.g., of from 2 to 6 carbon atoms, use of a vapor phase dehydration will be generally preferred in view of the high volatility of these alkanols. In contrast, liquid phase dehydration is preferred for aralkanols and cycloalkanols.

The conditions of temperature and pressure which can be employed can vary widely. Atmospheric pressure is most commonly employed. Dehydrations of high boiling alcohols, e.g., those with boiling points over 250° C. can be advantageously accomplished at pressures below atmospheric, or with a diluent gas, such as $N_2$, $CH_3$, $CO_2$, Ar and the like. The temperatures employed depend on the structure of the alcohol to be dehydrated. The ranges are summarized below:

| Type | Broad Range °C. | Preferred Range °C. |
|---|---|---|
| Primary Alkanol | 200-450 | 250-350 |
| Secondary Alkanol | 150-400 | 200-300 |
| Tertiary Alkanol | 80-250 | 125-175 |
| Cycloalkanol | 150-400 | 250-350 |
| Primary Aralkanol | 200-450 | 250-350 |
| Secondary Aralkanol | 110-400 | 200-300 |
| Tertiary Aralkanol | 100-300 | 125-250 |

In any dehydration process employing a liquid phase reaction medium, the temperature can be outside the aforementioned ranges, provided the temperature employed is below the decomposition temperature of the liquid phase reaction medium. Decomposition temperature, as herein used, refers to the temperature above which the rate of breakdown of the liquid phase reaction medium becomes appreciable (i.e., that the rate of decomposition of the liquid phase reaction medium equals or exceeds the rate of formation of the high-boiling residue) and, of course, depends on the nature of the reaction medium employed. When using stable high boiling hydrocarbons such as tri-phenylmethane (B.P.=359.2° C.) as the reaction medium, reaction temperatures of as much as 400° C. or more can be used using appropriate pressure. The decomposition characteristics of the high boiling residue formed in the dehydration reaction, which is a preferred liquid phase reaction medium, are such that it is desired to avoid temperatures above about 350° C. and it is preferred to avoid temperatures above about 330° C. In general, it is desired to employ reaction temperatures which are within the range of from about 220° C. to about 310° C. and it is preferred to employ reaction temperatures which are within the range of from about 250° C. to 300° C.

Since the dehydration reaction is endothermic, control of reaction temperature requires heat input to the reaction. Such can readily be provided by known techniques, for example, by inclusion of heating coils with the dehydration reactor.

It should be noted that, in general, lower reaction pressure favorably affects the reaction. Accordingly, it is desired to operate the process of this invention at as low a pressure as is feasible in the particular system employed. While either atmospheric, super-atmospheric or sub-atmospheric pressures can be used in the process of this invention, it is normally desired to employ pressures which are at or slightly above atmospheric. Though use of sub-atmospheric pressures further favors the desired reaction, it also increases the cost of construction of equipment and increases the danger of oxygen in-leakage which is both potentially hazardous and detrimental to the stability of the aralkene products. Accordingly, it is desired to operate the process of this invention at pressures which are between 15 psia and about 50 psia and it is preferred to operate the process of this invention at pressures which are between about 15 psia and 25 psia. As hereinabove indicated, substantially higher pressures can be used, for example as high as 250 psia or even higher, although when using such high pressures the conjoint use of an inert gas to reduce aralkanol partial pressure is greatly preferred. Similarly, it is also possible to operate the process of this invention at pressures which are as low as 0.1 psia or even lower, though it is seldom necessary to employ such low pressures.

When the improved dehydration process of this invention is conducted in the presence of a liquid phase reaction medium, substantially any high-boiling organic material can be used as the liquid phase reaction medium. By "high-boiling" as herein used is meant that the reaction medium boils at a temperature desirably at least 10° C. and preferably at least 30° C. above the temperature at which the alcohol, to be dehydrated boils. Suitable materials for use as liquid phase reaction media in this process include high boiling hydrocarbons such as tri-phenylmethane, anthracene, phenanthrene, high-boiling hydrocarbons petroleum distillates such as the while oils, the mineral oils and other suitable petroleum distillate cuts. Also suitable as liquid phase reaction mediums are such polar materials as the cresols, pyrocatechol, resorcinol, pyrogallol, 1,2,4-benzenetriol and phloroglucinol and their alkyl substituted derivatives. Similarly, suitable liquid phase reaction media for the dehydration of alkanols and cyclohexanols according to this invention are those listed above and biphenyl, diphenyl ether, and the like.

For aralkanol dehydrations, a particularly preferred liquid phase reaction medium is the high-boiling residue formed during the dehydration reaction itself since this material is indigenous to the process and available at substantially no cost. It is not practicable to characterize the nature of this material other than to say that it is believed to comprise polymers of the aralkene together with ether-type materials presumably formed by the reaction between two molecules of aralkanol. Since the selectivity of the dehydration in accordance with this invention is high, the residue is formed in only small quantity and it is therefore necessary to accumulate the residue either for batch or for continuous operation. In batch operation this presents slight difficulty since sufficient residue can be accumulated during the conduct of prior batch dehydration cycles. In continuous operation, however, it is normally necessary to start operations using an extraneous high-boiling reaction medium (sometimes referred to as a "heel"). As residue accumulates during subsequent operation, the heel is gradually displaced and replaced by the residue until, after a period of operation, the liquid phase reaction medium consists essentially of the residue without any significant amount of the heel remaining.

While the high-boiling residue formed in the reaction is the preferred liquid phase reaction medium for aralkanol dehydration in accordance with this process, it suffers from the drawback that, under reaction conditions, it foams excessively. This drawback is readily overcome by addition of a small amount of phenol or phenolic material to the liquid phase reaction medium.

Addition of as little as 200 ppm (by weight) of phenol or phenolic material present in the liquid phase reaction medium is effective to suppress the foaming. As much as 10%, or even more, can be used, although use of amounts of phenolic material in excess of about 2% appears to offer no advantage and may complicate product recovery. It is preferred to employ amounts of phenolic material between about 0.2% and about 2% by weight of the liquid phase reaction medium to suppress the foaming characteristics of the high-boiling residue. Suitable phenolic materials for this purpose include phenol itself, the cresols and other alkyl-substituted phenols, e.g., p-isopropylphenol and o-(n-hexyl)phenol, pyrocatechol, resorcinol, pyrogallol, 1,2,4-benzenetriol, phloroglucinol and the like. Phenol and the cresols are preferred since they are the cheapest and most readily available. During the dehydration, the phenolic material reacts in an, as yet, undefined manner, presumably to form etheric materials and consequently must be replaced periodically or continuously. Phenol itself and the cresols, the preferred antifoaming agents, have substantial volatility at reaction conditions and are partially vaporized along with the aralkene product. When using phenol as the anti-foaming agent, about 20% of the phenol added can be volatilized in this manner.

The high-boiling residue produced in aralkanol dehydration to aralkenes by the process of this invention can be treated by the method disclosed in Ser. No. 870,543, filed Jan. 16, 1978, for conversion of the high-boilers to additional amounts of aralkenes.

During the course of the reaction, the alcohol reacts to form water and the desired unsaturated organic product. When the alcohol is reacted in the presence of a liquid medium, the water and the unsaturated organic product which are formed are preferably volatilized substantially as rapidly as they are formed and are therefore readily removed from the reaction vessel. The alcohol, which can also be volatilized as the reaction proceeds, is preferably condensed and returned to the reaction vessel to effect the desired degree of conversion, i.e., to effect conversions on the order of 90% or more. While some by-products which are formed in the reaction in small quantities may also be volatilized, the amount of such volatilized by-products is not objectionable since the overheads from the dehydration reaction may be facilely treated by known techniques to recover the desired unsaturated organic compound from any such by-products. Thus, the overheads may be condensed and passed to a subsequent distillation vessel in which distillative methods are used to separate and recover the desired unsaturated organic compound which is formed in the dehydration step. High-boiling by-products which remain unvolatilized can be purged from the liquid phase reaction medium, periodically or continuously, when such materials accumulate to an undesired extent.

In the presence of a liquid medium, the logical inference to draw is that the dehydration occurs in the liquid phase. This is, however, not necessarily so since the unsaturated organic compound which is produced and the water which are formed in the dehydration are volatilized as the reaction proceeds, and it is possible that the dehydration reaction occurs at the vapor-liquid interface. Accordingly, no representation is made herein with regard to the phase in which the dehydration reaction of the process of this invention occurs in the instance in which the liquid phase reaction medium is used.

The concentration of alcohol and unsaturated organic compound in any liquid phase reaction medium can vary over wide limits and can be controlled independently of reaction temperature by suitable adjustment of total system pressure and partial pressures. Lowering of the total system pressure reduces these concentrations in the liquid phase. Similarly, the introduction of vaporous materials which are inert under the reaction conditions also reduces concentrations in the liquid phase by reducing component partial pressures. Suitable inert vapors for this purpose include such materials as helium, neon, argon, methane, ethane, propane, carbon dioxide, nitrogen and the like in the dehydration of aralkanols. Preferred inert vapors in the dehydration of alkanols and cycloalkanols include $CO_2$, $N_2$, methane, and the like.

The following examples are further intended to illustrate this invention without limiting the scope thereof. Unless otherwise indicated, all parts and percents referred to in the following examples are on a weight basis. In the Examples that follow, the silylated dehydration catalysts are analyzed for degree of silylation by the following method: The sample of the catalyst is fused with sodium peroxide and leached with water. The filtrate is acidified with hydrochloric acid, perchloric acid is added and the resulting mixture is heated until it fumes. The residue is diluted with water, and filtered to recover the precipitate. The solid is ignited in Pt crucible, weighed, treated with HF, reignited and weighed to determine weight loss from formation of volatile $SiF_4$. The degree of silylation is reported in the Examples as weight percent Si in the silylated dehydration catalyst.

EXAMPLE 1

An alumina catalyst, Catapal SB (manufactured by Continental Oil Company), having the composition noted in Table I above, is placed in a furnace and heated at 150° C. for 16 hours, followed by heating at 500° C. for 20 hours. Upon completion of this drying treatment, the catalyst is allowed to cool to room temperature and 10 grams of the dried catalyst is then charged to a glass tube provided with a glass frit and with a gas inlet and outlet, and which is in turn placed in a furnace for heating. Temperature is determined on the outside of the glass tube. The solid catalyst in the tube is then fluidized by passing nitrogen gas stream (20 l./hr.) through the tube and the furnace is heated to a temperature of 350° C. On reaching this temperature, dimethyldiethoxysilane is introduced to the tube at the rate of about 4 grams per hour by passing the nitrogen gas first through a sparger charged with dimethyldiethoxysilane in liquid form at room temperature. After contacting the alumina with the silylating agent for a period of 10 minutes, the reactor is cooled to room temperature while maintaining an atmosphere of nitrogen over the silylated dehydration catalyst. Analysis of the silylated dehydration catalyst thereby produced shows a Si content of 1.0 weight percent.

One gram of silylated dehydration catalyst produced as above is then charged in finely divided form to a glass vessel to which is also charged a solution containing 80 grams of alpha-phenyl ethanol and 232 grams of dry pseudocumene. This mixture is then heated to a pot temperature of 170° C. and under atmospheric pressure. No reflux is returned to the flask, for ease of operation. Water formed in the flask via dehydration of the alpha-phenyl ethanol is removed in the overhead product as a pseudocumene-water azeotrope, and fresh dry pseudocumene is added as needed to maintain a constant liquid level in the flask. The distillation is performed for a period of 2 hours, with approximately 90 grams per hour distillate being taken as overheads. The overhead product so removed is condensed and sampled at 30 minute intervals and analyzed for water, after being made homogeneous by addition of acetone, in order to determine the amount of water produced. The data thereby obtained are set forth in Table II below.

TABLE II

| Grams $H_2O$ Formed at: (hrs.) | | | |
|---|---|---|---|
| 0.5 | 1.0 | 1.5 | 2.0 |
| — | 0.36 | 0.64 | 0.9 |

EXAMPLE 2 FOR COMPARISON

The procedure of Example 1 is repeated except that the Catapal SB following the drying step is employed as the dehydration catalyst and is not contacted with any silylating agent. The catalyst is found to have a Si content of only 0.1 wt. %. Analysis of the overheads recovered during dehydration employing this catalyst yields the data set forth in Table III below.

TABLE III

| Grams $H_2O$ Formed at: (hrs.) | | | |
|---|---|---|---|
| 0.5 | 1.0 | 1.5 | 2.0 |
| 0.15 | 0.25 | 0.51 | 0.67 |

Thus, treatment of the Catapal SB alumina with the silylating agent in accordance with Example 1 to incorporate about 0.9 wt. % additional silica from the silylating agent produces a silylated dehydration catalyst which effects an activity increase of about 34%, based on the amount of water produced after 2 hours of dehydration, in comparison to the non-silylated alumina dehydration catalyst of the prior art.

EXAMPLE 3

The procedure of Example 1 is repeated except that the Catapal SB alumina is contacted with the silylating agent for a period of 30 minutes. The data obtained following dehydration using the silylated dehydration catalyst thereby produced yields the data set forth in Table IV below.

TABLE IV

| Grams $H_2O$ Formed at: (hrs.) | | | |
|---|---|---|---|
| 0.5 | 1.0 | 1.5 | 2.0 |
| 0.58 | 1.0 | 1.54 | 2.0 |

Thus, the silylated dehydration catalyst effects an activity increase of about 206% when compared to the non-silylated dehydration catalyst of Example 2 after 2 hours of dehydration. Analysis of the silylated dehydration catalyst shows a Si content of 1.96 wt. %. Thus, the foregoing increase in dehydration activity results from the addition to the alumina by the silylating agent of 1.86 wt. % Si.

EXAMPLE 4

The procedure of Example 1 is repeated except that the Catapal SB alumina is contacted with the silylating agent for a period of 60 minutes to produce a silylated dehydration catalyst which, when employed in the dehydration of the alpha-phenylethanol, yields the data set forth in Table V below.

TABLE V

| Grams $H_2O$ Formed at: (hrs.) | | | |
|---|---|---|---|
| 0.5 | 1.0 | 1.5 | 2.0 |
| 1.6 | 3.0 | 3.6 | 4.0 |

The silylated dehydration catalyst thereby produced effects an activity increase of 497% when compared to the non-silylated dehydration catalyst of Example 2, based on 2 hours of dehydration. Analysis of the silylated dehydration catalyst shows a Si content of 3.64 wt.%. Thus, the foregoing increase in dehydration activity results from the addition to the alumina by the silylating agent of 3.54 wt.% Si.

EXAMPLE 5

The procedure of Example 1 is repeated except that the Catapal SB alumina is contacted with the silylating agent for a period of 120 minutes to produce a silylated dehydration catalyst which, when employed in the dehydration of the alpha-phenylethanol, yields the data set forth in Table VI below.

TABLE VI

| Grams $H_2O$ Formed at: (hrs.) | | | |
|---|---|---|---|
| 0.5 | 1.0 | 1.5 | 2.0 |
| 1.9 | 4.2 | 5.5 | 6.6 |

The silylated dehydration catalyst thereby produced effects activity increase of 885% when compared to the non-silylated dehydration catalyst of Example 2, based on 2 hours of dehydration.

EXAMPLE 6

Ten grams of Catapal SB alumina which is dried according to the procedure of Example 1 is charged at room temperature to a glass tube provided with a glass frit and with a gas inlet and outlet, and which is in turn placed in a furnace for heating. The solid catalyst in the tube is then fluidized by passing a gas mixture through the tube and the furnace is heated to 400° C., determined as in Example 1. The gas mixture is continuously passed through the glass tube for a period of 2 hours after the 400° C. temperature is reached. The gas mixture so employed in contacting the catalyst comprises a $N_2$ gas stream which is first passed at a rate of 20 l./hr. through a sparger charged with dimethyldiethoxy silane, thereby passing the silylating agent to the glass tube at the rate of about 4 gms/hr. Thus, the alumina catalyst in this run is contacted with the silylating agent during the period in which the catalyst is heated from room temperature as well as during the period in which the catalyst is maintained at the selected temperature.

After recovering the resulting silylated dehydration catalyst using the procedure of Example 1, the silylated catalyst is employed in the dehydration of alpha-phenyl ethanol as in Example 1, thereby yielding the date set forth in Table VII below:

TABLE VII

| Grams H₂O Formed at: (hrs.) | | | |
|---|---|---|---|
| 0.5 | 1.0 | 1.5 | 2.0 |
| 5.1 | 10.1 | 11.0 | 11.3 |

The silylated dehydration catalyst thereby produced effects activity increase of 1.586% when compared to the non-silylated dehydration catalyst of Example 2, based on 2 hours of dehydration.

EXAMPLE 7

The procedure of Example 1 is repeated for treatment of Catapal SB alumina except that 4.4 milliters per hour of trimethylchlorosilane are vaporized into the nitrogen gas stream (20 liters per hour), and the silylating treatment is continued over a period of 3 hours. The silylated dehydration catalyst thereby produced is found to contain 3.3 wt. % Si, with 3.2 wt. % Si thus being introduced to the catalyst by the silylating agent. Use of the silylated dehydration catalyst thereby produced in the dehydration of alphaphenylethanol as described in Example 1 yield the data set forth in Table VIII.

TABLE VIII

| Grams H₂O Formed at: (hrs.) | | | |
|---|---|---|---|
| 0.5 | 1.0 | 1.5 | 2.0 |
| 0.19 | 0.71 | 1.05 | 1.41 |

Thus, the silylated dehydration catalyst effects a 110% increase in activity for dehydration, based on the data obtained after 2 hours, when compared to the non-silylated catalyst of Example 2.

EXAMPLE 8

The procedure of Example 1 is repeated except that 1.4 milliliters per hour of triethylchlorosilane are vaporized into the nitrogen gas stream (20 liters per hour), and the silylating treatment is continued for a period of 5.5 hours. Analysis of the silylated dehydration catalyst thereby obtained shows the catalyst to contain 2.7 wt.% Si, with 2.6 wt.% Si therefore being introduced by treatment of the alumina with the silylating agent. Use of the silylated dehydration catalyst thereby produced in the dehydration of alphaphenylethanol as described in Example 1 yields the data set forth in Table IX below.

TABLE IX

| Grams H₂O Formed at: (hrs.) | | | |
|---|---|---|---|
| 0.5 | 1.0 | 1.5 | 2.0 |
| 0.61 | 0.35 | 1.55 | 2.58 |

Thus, the silylated dehydration catalyst effects a 285% increase in the rate of dehydration, based on data obtained after 2 hours, when compared to the non-silylated catalyst of Example 2.

EXAMPLE 9

The procedure of Example 1 is repeated except that the alumina employed is Alcoa Grade F-1 (manufactured by Aluminum Company of America, minus 325 mesh) having the composition noted in Table I above. After treatment for a period of 3 hours with dimethyldiethoxysilane introduced via a nitrogen gas stream as described in Example 1, the silylated dehydration catalyst produced is found to have a Si content of 3.3 wt.%. The Alcoa Grade F-1 alumina, prior to treatment with the silylating agent, is analyzed and found to contain only 0.7 wt.% Si. Thus, the silylating treatment incorporated an additional 2.6 wt.% Si into the alumina.

Use of the silylated dehydration catalyst thereby produced in the dehydration of alpha-phenylethanol as in Example 1 yields the data set forth in Table X below.

TABLE X

| Grams of H₂O Formed at: (hrs.) | | | |
|---|---|---|---|
| 0.5 | 1.0 | 1.5 | 2.0 |
| 0.26 | 0.58 | 0.94 | 1.3 |

To determine the rate of dehydration using non-silylated catalyst, the foregoing dehydration is repeated except that the dehydration catalyst used comprises Alcoa Grade F-1 alumina which, following the drying step used in Example 1, is not contacted with any silylating agent. The data obtained following dehydration of alpha-phenylethanol as in Example 1 using this non-silylated catalyst is set forth in Table XI below.

TABLE XI

| Grams H₂O Formed at: (hrs.) | | | |
|---|---|---|---|
| 0.5 | 1.0 | 1.5 | 2.0 |
| 0.06 | 0.15 | 0.19 | 0.28 |

Thus, the silylated dehydration catalyst effects 364% increase in the rate of dehydration when compared to the non-silylated catalyst (based on data obtained after 2 hours of dehydration).

EXAMPLE 10

Following the procedure of Example 1, 50 ml. Alcoa Grade H-151 alumina (⅛ inch spheres; manufactured by Aluminum Company of America) having the composition noted in Table I above, is silylated by contacting the alumina with 1.4 milliters per hour of triethylchlorosilane, vaporized into 20 liters per hour of gaseous nitrogen, at 315° C. for a period of 6 hours. The silylated dehydration catalyst thereby produced is then employed in the vapor phase dehydration of ethanol, which is effected by vaporizing 29 milliliters per hour of ethanol into 10 liters per hour of nitrogen to form a gas mixture which is passed over 25 ml. of the silylated dehydration catalyst at a temperature of 350° C. in a tubular reactor. The gas exiting the reactor is passed through an ice trap to condense any water present in the exit gases, and the noncondensed gases comprising the vapor effluent from the ice trap is then analyzed for ethylene content. In a separate step, the above procedure is repeated except that the catalyst used in the dehydration comprises Alcoa Grade H-151 alumina which has been oven-dried at 350° C. for a period of 5 hours and which has not been contacted with any silylating agent. The effluent gas from the run using the silylated dehydration catalyst is found to contain 24 wt.% ethylene, whereas this gas in the run using the non-silylated control catalyst is found to contain only 19 wt.% ethylene. Thus, the silylated dehydration catalyst effects a 26.3% increase in the rate of dehydration of the ethanol.

EXAMPLE 11

A silylated dehydration catalyst is prepared as in Example 10 except that the silylating agent comprises dimethyldiethoxysilane and the treatment time with the silylating agent is 3 hours. The silylated dehydration catalyst so produced is then employed in the vapor phase dehydration of isopropanol which is effected by vaporizing 29 milliliters per hour of isopropanol into 10 liters per hour of gaseous nitrogen to form a gas mixture which is then passed over 25 ml. of the silylated dehydration catalyst at a temperature of 250° C. in a tubular reactor. As in Example 10, the gases exiting the reactor are passed first through an ice trap and then analyzed for the propylene content of the effluent gas. As a control, Alcoa Grade H-151 alumina which has been oven dryed at 350° C. for a period of 5 hours and which has not been contacted with any silylating agent is employed as catalyst in a separate run for dehydration of isopropanol by the above procedure. Analysis of the effluent gas in the run using the silylated dehydration catalyst shows an propylene content in the effluent gas of 15.5 wt.%, whereas the effluent gas only contained 9.7 wt.% propylene in the control run which employed the non-silylated dehydration catalyst. Thus, use of the silylated dehydration catalyst effects a 59.8 percent increase of the dehydration of the isopropanol.

EXAMPLE 12

The procedure of Example 10 is repeated except that the silylated dehydration catalyst and the control catalyst are employed in separate runs in the dehydration of tertiary butyl alcohol which is effected by vaporizing 58 milliliters per hour of the tertiary butyl alcohol into 20 liters per hour of gaseous nitrogen to form a gas mixture which is passed over the selected catalyst at a temperature of 150° C. Analysis of the effluent gas in each run shows the silylated dehydration catalyst to effect an increase in the rate of dehydration over the non-silylated catalyst similar to that observed in Example 10.

It will be obvious that various changes and modifications may be made without departing from the invention and it is intended, therefore, that all matter contained in the foregoing description shall be interpreted as illustrative only and not limitative of the invention.

I claim:

1. A process for the catalytic dehydration of an alcohol to an unsaturated organic compound which comprises contacting the alcohol under dehydration conditions with a silylated dehydration catalyst formed by treatment of an alumina having a surface area of at least about 15 square meters per gram at elevated temperatures with at least one organic silylating agent selected from the group consisting of compounds having the formula:

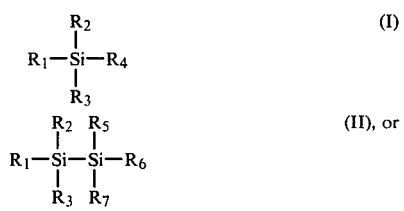

wherein X is oxygen or

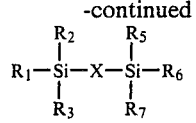

and $R_1$, $R_2$, $R_3$, $R_4$, $R_5$, $R_6$ and $R_7$ are independently selected from the group consisting of hydrogen, hydroxy, halogen, alkoxy of from 1 to 8 carbon atoms, alkyl of from 1 to 8 carbon atoms, aryl of from 6 to 12 carbon atoms, alkenyl of from 2 to 8 carbon atoms, alkyl-substituted aryloxy having a total of from 7 to 12 carbon atoms, aryloxy of from 6 to 12 carbon atoms, aryl-substituted alkoxy of from 7 to 12 carbon atoms, alkaryl and aralkyl of from 7 to 12 carbon atoms, amino, acyl of from 1 to 8 carbon atoms and acyloxy of from 1 to 8 carbon atoms, with the proviso that at least one of $R_1$, $R_2$, $R_3$, $R_4$, $R_5$, $R_6$ and $R_7$ must be alkyl, aryl, aralkyl, alkaryl, alkenyl or acyl, and with the further proviso that if the silicon compound is characterized by formula (I) or (II) above, at least one or $R_1$, $R_2$, $R_3$, $R_4$, $R_5$, $R_6$ and $R_7$ must be hydroxy, halo, alkoxy, alkyl-substituted aryloxy, aryl-substituted alkoxy, aryloxy, amino, acyloxy, or cycloalkoxy.

2. The process according to claim 1 wherein the silylating agent comprises at least one member selected from the group consisting of compounds having the formula:

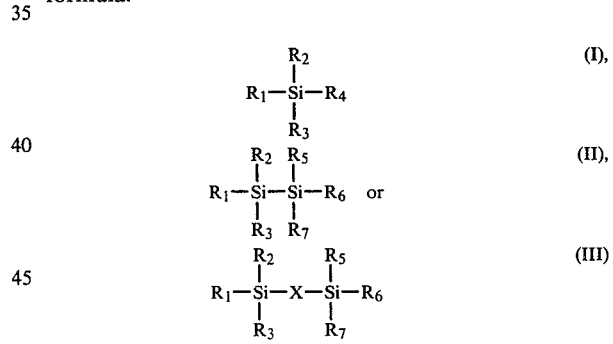

wherein X is oxygen or

and $R_1$, $R_2$, $R_3$, $R_4$, $R_5$, $R_6$ and $R_7$ are independently selected from the group consisting of hydrocarbyl of from 1 to 4 carbon atoms, halo and alkoxy of 1 to 6 carbon atoms, with the proviso that when the silylating agent comprises a compound of formula (I) or (II), at least one of $R_1$, $R_2$, $R_3$, $R_4$, $R_5$, $R_6$ and $R_7$ must be hydrocarbyl and at least one of $R_1$, $R_2$, $R_3$, $R_4$, $R_5$, $R_6$ and $R_7$ must be halo or alkoxy.

3. The process according to claim 1 wherein the silylated dehydration catalyst contains at least about 0.05 weight percent Si greater than the Si content of the alumina which is treated with the silylating agent.

4. The process according to claim 1 wherein the silylating agent comprises a member selected from the group consisting of trimethyl ethoxysilane, triethyl methoxysilane, methyl-di(n-propoxy)silane, benxyl-di(n-butoxy)silane, isopropyl triacetoxysilane, methyltriethoxysilane, chlorophenylphenoxysilane, tolyldibenzoxysilane, aminopropyltriethoxysilane, vinyltrichlorosilane, trimethylacetoxysilane, dimethyldipropoxysilane, dichlorodimethoxysilane, chlorotrimethoxysilane, N-methyl-3-amino-propyltrimethoxysilane, N-methyl-N-octadecyl-3-aminopropyltriethoxysilane, chlorobromomethylethoxysilane, chlorodiethylcyclohexoxysilane, iododimethylbutoxysilane, chlorodimethylphenoxysilane, dimethyldiethoxysilane, methyltrimethoxysilane, phenyltrimethoxysilane, dimethyldi(meta-toloxy)silane, sym. tetrachlorodimethoxydisilane, sym. difluorodiphenoxydisilane,

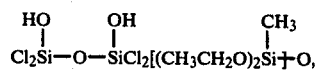

hexamethyldisilazane, and sym. tetramethyldisilazane.

5. The process according to claim 1 wherein the alcohol comprises a primary alkanol and wherein said catalytic dehydration is effected at a temperature of from about 200° to 450° C.

6. The process according to claim 1 wherein the alcohol comprises a secondary alkanol and wherein said catalytic dehydration is effected at a temperature of from about 150° to 400° C.

7. The process according to claim 1 wherein the alcohol comprises a tertiary alkanol and wherein said catalytic dehydration is effected at a temperature of from about 80° to 250° C.

8. The process according to claim 1 wherein the alcohol comprises cycloalkanol and wherein said catalytic dehydration is effected at a temperature of from about 150° to 400° C.

9. The process according to claim 1 wherein the alcohol comprises a primary aralkanol and wherein said catalytic dehydration is effected at a temperature of from about 200° to 450° C.

10. The process according to claim 1 wherein the alcohol comprises a secondary aralkanol and wherein said catalytic dehydration is effected at a temperature of from about 110° to 400° C.

11. The process according to claim 1 wherein the alcohol comprises a tertiary aralkanol and wherein said catalytic dehydration is effected at a temperature of from 100° to 300° C.

* * * * *

UNITED STATES PATENT AND TRADEMARK OFFICE
CERTIFICATE OF CORRECTION

PATENT NO. : 4,207,424
DATED : June 10, 1980
INVENTOR(S) : Charles N. Winnick

It is certified that error appears in the above-identified patent and that said Letters Patent are hereby corrected as shown below:

Col. 1, line 31 - "a" should be --the--

Col. 8, line 29 - "while" should be --white--

Col. 12, line 67 - "date" should be --data--

Col. 13, line 9 - "1.586%" should be --1,586%--

Col. 13, line 15 - "milliters" should be --milliliters--

Col. 14, line 44 - "milliters" should be --milliliters--

Col. 15, line 24 - "an" should be --a--

Col. 16, line 27 - "one or $R_1$" should be --one of $R_1$--

Signed and Sealed this

Twenty-third Day of February 1982

[SEAL]

Attest:

Attesting Officer

GERALD J. MOSSINGHOFF

Commissioner of Patents and Trademarks